United States Patent
Matsuda et al.

[11] Patent Number: 6,087,672
[45] Date of Patent: Jul. 11, 2000

[54] CHARGED PARTICLE BEAM IRRADIATION SYSTEM AND IRRADIATION METHOD THEREOF

[75] Inventors: Koji Matsuda; Hiroshi Akiyama, both of Hitachi; Kazuo Hiramoto, Hitachiota, all of Japan

[73] Assignee: Hitachi, Ltd., Tokyo, Japan

[21] Appl. No.: 09/106,905

[22] Filed: Jun. 30, 1998

[30] Foreign Application Priority Data

Mar. 7, 1997 [JP] Japan .................................... 9-178048

[51] Int. Cl.⁷ .................................. G21K 1/00; H01J 1/52
[52] U.S. Cl. .................................... 250/505.1; 250/515.1; 250/492.3; 378/156; 378/159
[58] Field of Search ............................. 250/505.1, 515.1, 250/492.22, 492.3; 378/156, 159

[56] References Cited

U.S. PATENT DOCUMENTS

5,969,367  10/1999  Hiramoto et al. .................. 250/492.3

*Primary Examiner*—Bruce C. Anderson
*Assistant Examiner*—Nikita Wells
*Attorney, Agent, or Firm*—Antonelli, Terry, Stout & Kraus, LLP

[57] ABSTRACT

A charged particle beam irradiation system includes a beam spreading device, a ridge filter, a range shifter, a collimator, and a bolus. Further, on a supporting plate in the ridge filter, a plurality of ridge components are arranged, and shielding elements are attached at the top parts of a part of the plurality of the ridge components.

6 Claims, 10 Drawing Sheets

CHARGED PARTICLE BEAM

CHARGED PARTICLE BEAM IRRADIATION SYSTEM AND IRRADIATION METHOD THEREOF

BACKGROUND OF THE INVENTION

The present invention relates to a charged particle beam irradiation system for irradiating a charged particle beam onto a target and a method of beam irradiation; and, especially, the invention relates to a charged particle beam irradiation method and system in which the shape and intensity of the charged particle beam can be controlled in accordance with the three-dimensional shape of a target to be irradiated.

A charged particle delivery system is a system for forming a field for irradiation of a target by a charged particle beam in accordance with the three-dimensional shape of the target and for adjusting the distribution of the dose in the irradiation field.

Such a charged particle beam delivery system consists of a lateral direction beam shaping part for establishing an irradiation range in a plane perpendicular to the direction of the charged particle beam, and a trajectory direction beam adjusting part for adjusting the irradiation range in the direction of the charged particle beam (in the depth direction of the target). The lateral direction beam shaping part spreads the charged particle beam on a plane perpendicular to the direction of the charged particle beam and shapes the spread of the charged particle beam in accordance with the shape of the target projected on a plane perpendicular to the direction of the beam by cutting out the spread beam using a collimator. Further, the trajectory direction beam adjusting part adjusts the energy range of the charged particle beam in accordance with the cross-sectional shape of the target in the direction of the beam (in the depth direction of the target). A conventional charged particle beam delivery system of this type is disclosed on pages 2055–2122 of No. 8 (August, 1993) in Vol. 64 of "Review of Scientific Instruments".

For charged particle irradiation therapy, it is desirable to produce a conformal irradiation in which the irradiation is performed in accordance with the three-dimensional shape of a diseased part by irradiating a high dose of energy on the diseased part and a low dose of energy on parts other than the diseased part. As a conventional conformal irradiation method, a scanning method which scans a diseased part with a thin charged particle beam, a method of irradiating a diseased part with a charged particle beam by dividing the diseased part in layers using a multi-leaf collimator, etc. has been used. Japanese Patent Application Laid-Open 148277/1995 discloses a conformal irradiation method in which a beam is irradiated onto a diseased part by using a uneven ridge filter and a multi-collimator.

A conformal irradiation system using the scanning method becomes complicated since it is necessary to control the beam, as well as to measure the dose of the beam at a high speed and with a high accuracy. Also, a conformal irradiation apparatus using the method of irradiating a charged particle beam by dividing the diseased part in layers or the method using a uneven ridge filter becomes complicated since it is necessary to properly control a multi-leaf collimator with a required timing.

SUMMARY OF THE INVENTION

An object of the present invention is to provide a charged particle beam irradiation system and an irradiation method for use therein, which can adjust the energy distribution of a charged particle beam and irradiate the beam onto a target with a uniform dose rate of distribution.

The first feature to attain the above-mentioned object of the present invention is to provide a charged particle beam irradiation system for irradiating a charged particle beam, which includes a plurality of charged particles in an energy range, onto a target having a non-uniform depth distribution in its cross section in the charged particle beam irradiation direction, and further including a plurality of ridge components and shielding elements to shield a part of the charged particle beam over an area corresponding to a thin region in the target. Since the energy distribution and the particle density of the charged particle beam irradiated onto the target can be adjusted by shielding part of the charged particle beam, it is possible to irradiate the charged particle beam onto a target in accordance with the shape of the target with a uniform dose distribution. Therefore, it becomes possible to safely increase the dose of the beam irradiated onto the target, and further, to suppress the dose of the beam irradiated on a part other than the target region. In this regard, the depth of the target refers to the depth in a cross section of the target in the beam (irradiation) direction.

A second feature to attain the above-mentioned object of the present invention is that, in the charged particle beam irradiation system, shielding elements are composed and arranged so that the difference between the maximum energy and the minimum energy of charged particles in the charged particle beam irradiated onto a comparatively thick region of the target is larger than the difference between the maximum energy and the minimum energy of charged particles in the charged particle beam irradiated onto a comparatively thin region of the target. Since the charged particle beam can be irradiated onto the target in accordance with its shape by adjusting the energy range of the charged particle beam with the shielding elements, according to the thickness distribution in the target, it is possible to increase the dose of the beam irradiated onto the target and suppress the dose of the beam irradiated on a part other than the target region.

A third feature to attain the above-mentioned object of the present invention is that, in the charged particle beam irradiation system, the shielding elements are attached to a part of ridge components through which a charged particle beam is irradiated onto a comparatively thin region of the target. Since the shielding elements are attached to a part of the ridge components, and the shielding elements are supported by the ridge filter, it is not necessary to provide means for independently supporting the shielding elements. Thus, the composition of the charged particle beam irradiation system becomes simple.

A fourth feature to attain the above-mentioned object of the present invention is to provide a charged particle beam irradiation system having a ridge filter for irradiating a charged particle beam, which includes a plurality of charged particles in an energy range, onto a target having a non-uniform depth distribution in its cross section in the charged particle beam irradiation direction, wherein the ridge filter, which is placed along a trajectory of the charged particle beam, includes a plurality of ridge components having different height values, and a plurality of shielding elements are provided to shield a part of the charged particle beam passing through comparatively low ridge components of the plurality of ridge components. By placing the ridge filter, which includes a plurality of ridge components having different height values, along a trajectory of the charged particle beam, it is possible to adjust the energy distribution of the charged particle beam according to the shape of the target. Further, by providing a plurality of shielding elements to shield a part of the charged particle beam, it is possible to adjust the particle density distribution of the charged particle beam. Therefore, it is possible to irradiate the charged particle beam onto a target in accordance with the shape of the target and with a uniform dose distribution. Thus, it becomes possible to increase the dose of the beam irradiated on the target and to suppress the dose of the beam irradiated on a part other than the target region.

A fifth feature to attain the above-mentioned object of the present invention is to provide a charged particle beam irradiation system for irradiating a charged particle beam, which includes a plurality of charged particles in an energy range, onto a target having an non-uniform depth distribution in its cross section in the charged particle beam irradiation direction, and further including beam adjustment means for adjusting the charged particle beam so that the difference between the maximum energy and the minimum energy of charged particles in the charged particle beam irradiated on a comparatively thick region of the target is larger than the difference between the maximum energy and the minimum energy of charged particles in the charged particle beam irradiated on a comparatively thin region of the target, the particle density of the charged particles in the charged particle beam irradiated on the comparatively thick region being higher than the particle density of the charged particles in the charged particle beam irradiated to the comparatively thin region. By adjusting the energy distribution and the particle density using the beam adjustment means, it is possible to irradiate the charged particle beam on a target in accordance with the shape of the target and with a uniform dose distribution. Thus, it becomes possible to increase the dose of the beam irradiated on the target and to suppress the dose of the beam irradiated on a region other than the target region.

A sixth feature to attain the above-mentioned object of the present invention is to provide a charged particle beam irradiation method of irradiating a charged particle beam, which includes a plurality of charged particles in an energy range, onto a target having an non-uniform depth distribution in its cross section in the charged particle beam irradiation direction, the method comprising the steps of arranging shielding elements at a part of the ridge components composing a ridge filter; placing the ridge filter along a trajectory of the charged particle beam; and irradiating the charged particle beam onto the target through the ridge filter. By arranging shielding elements at the part of the ridge components composing the ridge filter and placing the ridge filter along the trajectory of the charged particle beam, it is possible to adjust the energy distribution and the particle density with the beam adjustment means, and to irradiate the charged particle beam onto the target in accordance with the shape of the target and with a uniform dose distribution. Thus, it becomes possible to increase the dose of the beam irradiated on the target and to suppress the dose of the beam irradiated on a region other than the target region.

DETAILED DESCRIPTION OF THE EMBODIMENTS

Figure 1:
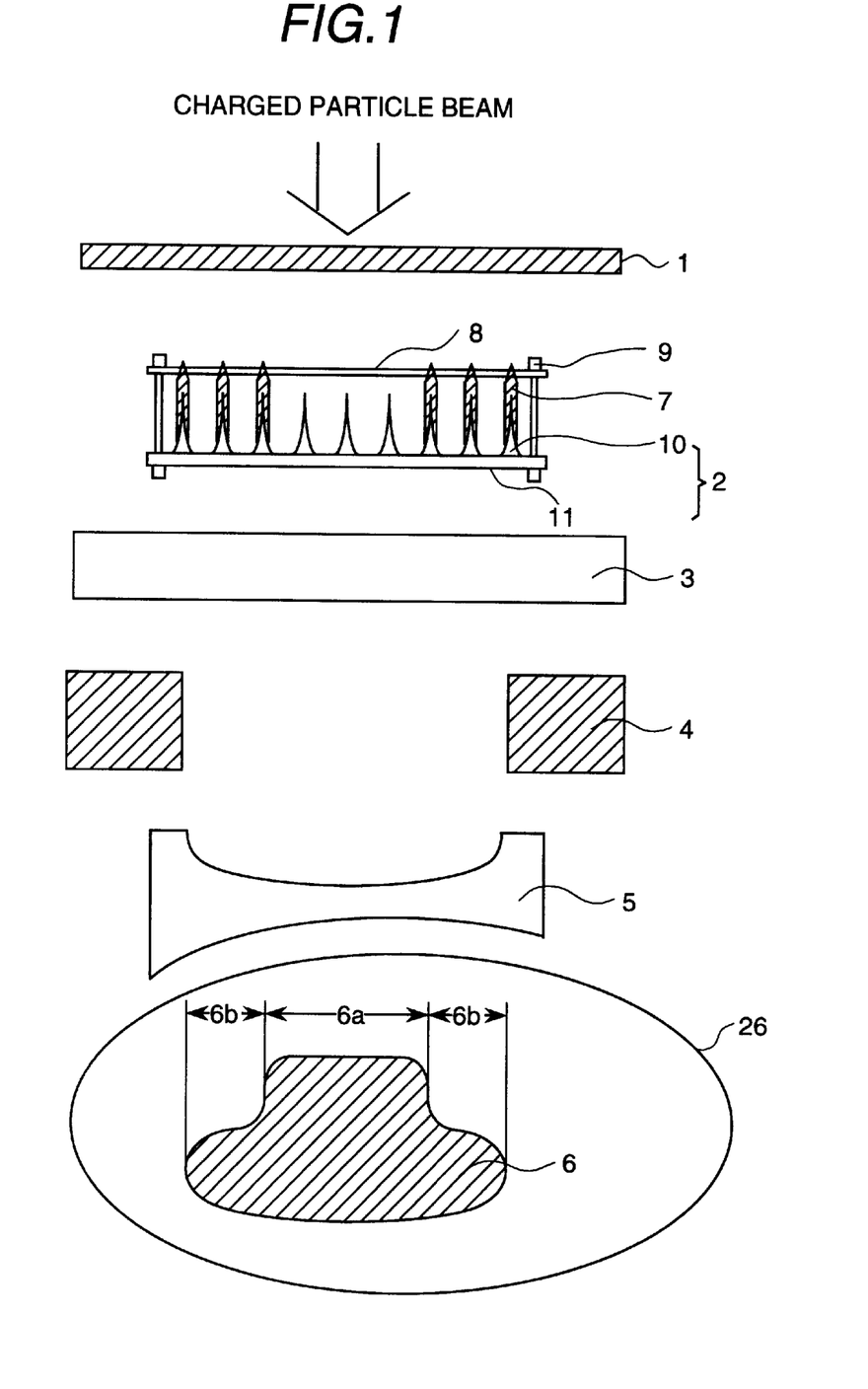
FIG. 1 is a schematic diagram showing the composition of a charged particle beam irradiation system forming a first embodiment of the present invention.

FIG. 1 is a schematic diagram showing the composition of a charged particle beam irradiation system representing a first embodiment according to the present invention. In this embodiment, the target is a diseased part 6 of irregular thickness. In this regard, as shown in FIG. 1, a front view of the target in the charged particle beam irradiation direction (hereafter, referred to simply as the beam direction) has a circular shape, and a cross section has a shape composed of a thick region at a central part and thin regions existing at both lateral sides in the beam direction. Herein, the energy of charged particles in a charged particle beam is simply expressed as the energy of the charged particle beam.

The charged particle beam irradiation system includes a beam spread device 1 for spreading the charged particle beam in a direction perpendicular to the beam direction, a ridge filter 2 for adjusting the energy distribution of the charged particle beam by changing the energy of charged particles passing through the ridge filter, a range shifter 3 for shifting the energy distribution of the charged particle beam, a collimator 4 for cutting out a desired part of the charged particle beam in accordance with the shape of a transverse cross section of the diseased part in the direction perpendicular to the beam direction, a bolus 5 for adjusting the energy of charged particles in the beam in coincidence with the maximum depth from the front surface of the diseased part 6, and shielding elements 7 arranged at the ridge filter 2.

The charged particle beam generated by a charged particle beam generation apparatus (not shown in a figure) is fed to the charged particle beam irradiation system from the top in FIG. 1, in the beam direction shown by the arrow. Further, the charged particle beam spread by the beam spread device 1 and adjusted by the ridge filter 2 is shaped in accordance with the cross-sectional area and the depth, that is, the three-dimensional shape, of the diseased part 6. Then, the shaped charged particle beam is irradiated onto the diseased part 6.

Figure 2:
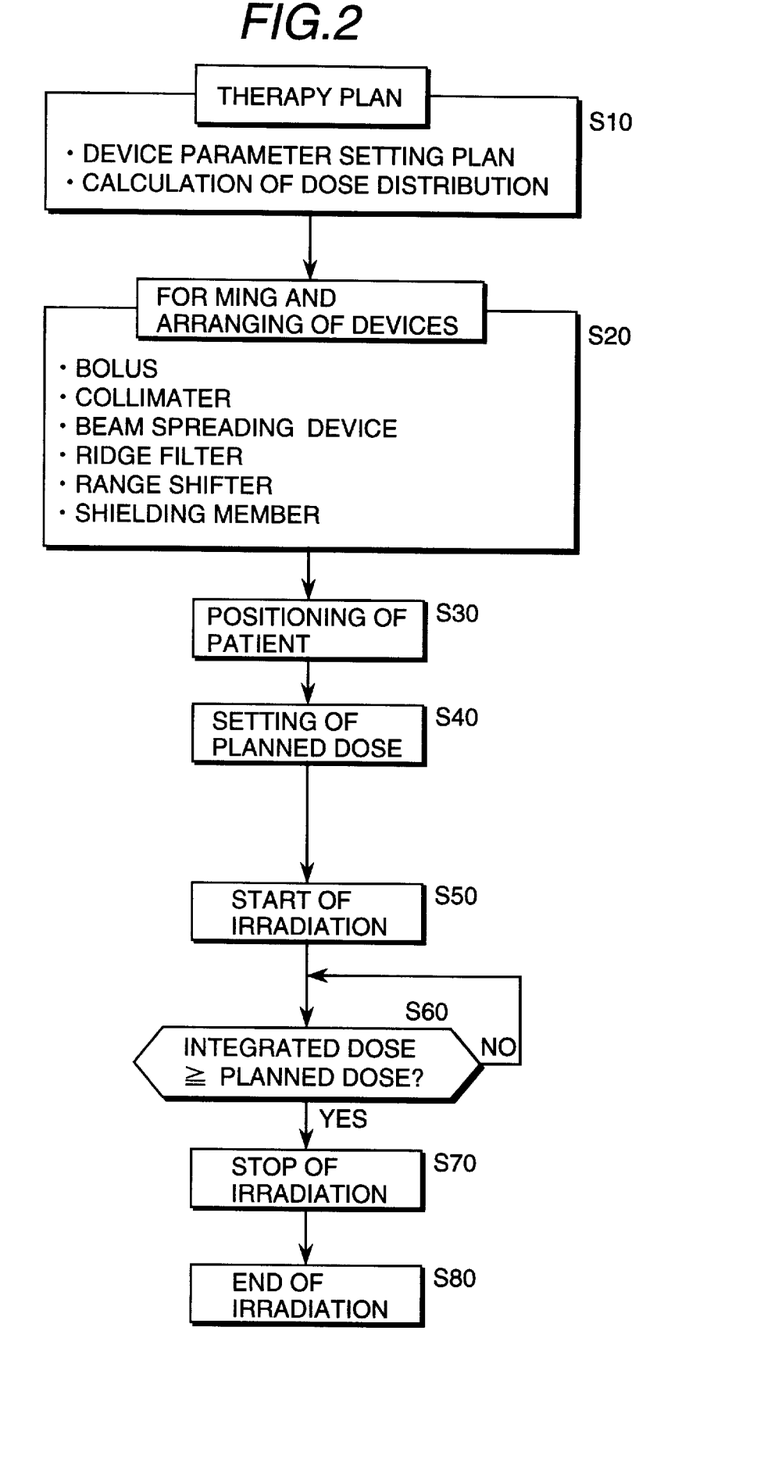
FIG. 2 is a flow chart of a beam irradiation process which uses the charged particle beam irradiation system shown in FIG. 1.

A method of irradiating the charged particle beam by using the charged particle beam irradiation system of this embodiment will be explained. FIG. 2 is a flow chart showing beam irradiation procedures which are used in this charged particle beam irradiation system. The substance of each step shown in the flow chart is as follows.

Step S10: The necessary energy range and the dose of a charged particle beam to irradiated onto a diseased part, the irradiation procedures, and so forth, are obtained on the basis of a computed analysis according to a therapy plan determined for each patient in advance. In this regard, parameters for setting up devices used in the irradiation system (the spreading power of an irradiation field formed by the beam spread device 1, the amount of shift in the energy distribution produced by the shifter 3, the height of each ridge component arranged in the ridge filter 2, etc.) are determined.

Step S20: Each device is set up according to the obtained parameters determined for the various devices in Step S10. The bolus 5, the collimator 4, the ridge filter 2, and the shielding elements 7, are formed in accordance with the three-dimensional shape of the diseased part. In this embodiment, the collimator 4 is formed for each diseased part, since the collimator 4 is required to correspond to the cross-sectional shape of the diseased part in a direction perpendicular to the beam direction. Moreover, the bolus 4 is formed for each diseased part in accordance with the maximum depth of the diseased part 6 in the beam direction. Finally, in the ridge filter 2, the shielding elements 7 are selectively cover the ridge components 10 in a pattern according to the depth and the shape of the diseased part 6.

Step S30: After the setting-up of each device is finished, the patient is positioned so that the charged particle beam will be irradiated onto the diseased part 6.

Step S40: The planned close of the charged particle beam to be irradiated onto the diseased part is set.

Step S50: Irradiation of the charged particle beam is started. Procedures for the irradiation are the same as those executed in a conventional irradiation method in which a conformal irradiation is not carried out.

Step S60: It is determined whether the irradiated dose has reached the planned dose.

Step S70: If the irradiated dose has reached the planned dose, the irradiation is stopped.

Step S80: The irradiation therapy is ended.

Hereupon, in the step S30, both the procedure for attaching the shielding elements 7 at the ridge filter 2 after the ridge filter 2 is placed along the trajectory of the charged particle beam, and the procedure for placing the ridge filter 2 along the trajectory of the charged particle beam after the shielding elements 7 are attached at the ridge filter 2, are applicable.

Figure 3A:
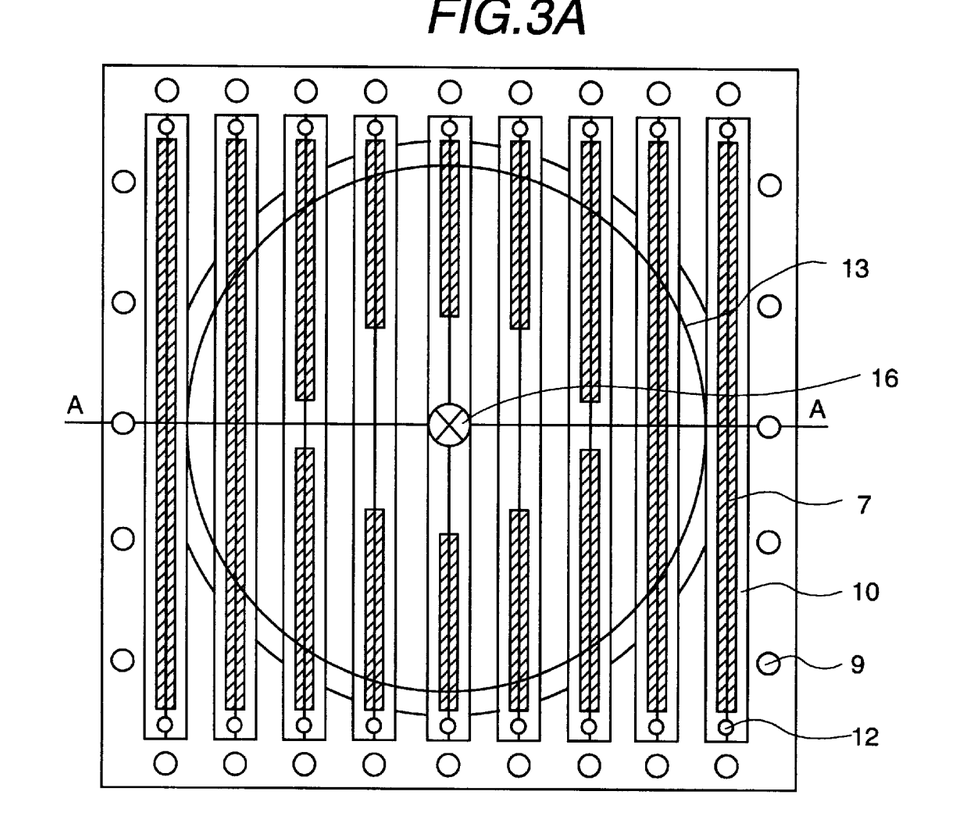
FIG. 3A and FIG. 3B are a front view and a sectional side elevation view, respectively, of an example of a ridge filter used in the charged particle beam irradiation system shown in FIG. 1.
Figure 3B:
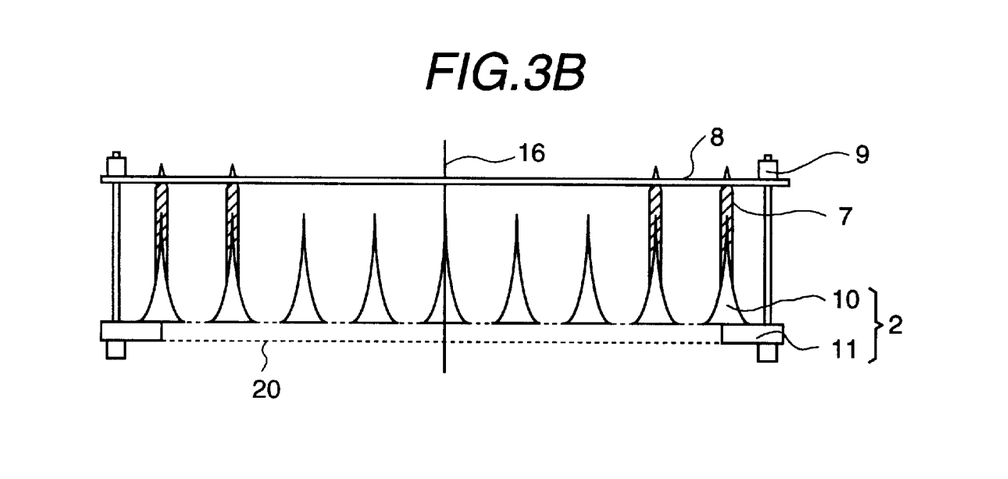

The ridge filter 2 and the shielding elements 7 in the charged particle beam irradiation system of this embodiment will be explained in more detail below. FIG. 3A and FIG. 3B are a front view and a sectional side elevation view, respectively, of the ridge filter 2 and the shielding elements 7 arranged at the ridge filter 2, used in the charged particle beam irradiation system shown in FIG. 1. The ridge filter 2 includes a plurality of ridge components 10 arranged and supported on a support plate 11, a circular hole being provided at the center of the support plate 11, and shielding elements 7 cover the top of parts of the ridge components 10. The plurality of the ridge components 10, each of which has a wedge-shaped vertical cross section, are arranged in parallel lines on the support plate with the sharp ridge line of each of the ridge components being directed upward, and these ridge components 10 are fixed to the supporting plate 11 with clasps 12. The shielding elements 7 are fixed in position at their upper end to the ridge filter 2 by means of a supporting plate 8 having slits into each of which the top part of each shielding element 7 is inserted, and the supporting plate 8 is secured by clasps 9. The numeral 13 indicates a region through which the beam spread by the beam spread device 1 passes, and numeral 16 indicates the central axis of the beam.

Figure 4:
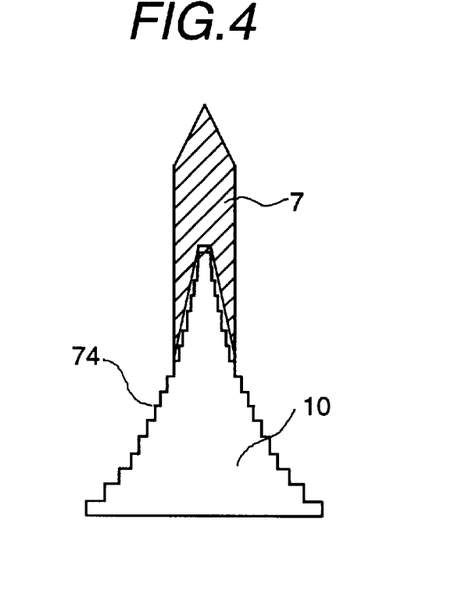
FIG. 4 is a vertical cross section of a ridge component to which a shielding element is attached.

Next, the combination of a ridge component 10 and a shielding element 7 will be explained further. FIG. 4 is a vertical cross section of a ridge component 10 on which a shielding element 7 is attached. The charged particle beam proceeds in the direction of the upper part to the lower part in FIG. 4. Since both sides of each ridge component 10 are formed in tiers, the thickness of the ridge filter 2 through which charged particles in the beam pass depends on the position in the filter at which the charged particles are injected.

Charged particles in the beam lose energy corresponding to the thickness of the part in the ridge component 10 through which the charged particles pass. Charged particles passing through a part having a larger thickness in the ridge component 10 lose more energy, and charged particles in the beam passing through a part of a smaller thickness in the ridge component 10 lose less energy. Therefore, charged particles in the beam will have a different energy depending on the thickness of the part in the ridge component 10 through which the charged particles pass. The distribution of energy of the charged particles is determined by the ratio of the area of each step in the side tiers of the ridge component 10 to the whole area of the sides. Therefore, the energy distribution (or energy range) of the charged particle beam passing through the ridge filter 2 is determined by the shape of each ridge component 10. A charged particle beam passing through a higher ridge component has a lower average value of energy in comparison with a beam passing through a lower ridge component.

The position in a target in the beam direction, which the charged particle beam can reach, that is, the depth in the target which the beam can reach, is determined by the energy of the beam. The higher the energy of the charged particle beam is, the deeper in the target the beam can reach, and vice versa.

If a charged particle beam to be irradiated on the diseased part 6 is formed by combining a plurality of charged particle beams having different energy levels, the range (depth) in the target in the beam direction, to which the combined charged particle beam can be irradiated (proceed), is a range obtained by overlapping of respective distances which the respective charged particle beams can reach. The range of irradiation in the depth direction is wider as the energy range in a charged particle beam is wider, and vice versa.

Since a charged particle beam which has passed through the ridge component 10, the sides of which are in tiers, includes charged particles of various energy levels, the energy distribution of the original charged particle beam is widened. Therefore, the range of irradiation becomes wider.

A charged particle beam passing through the shielding element 7 losses a large amount of energy, and its average energy level becomes low. Therefore, the beam is stopped in the shielding element 7, or devices existing downstream thereof, and does not reach the diseased part 6. In considering a beam passing through a ridge component 10 covered by a shielding element 7 and a beam passing through a ridge component 10 without a shielding element 7, it is apparent that these beams do not have the same energy as charged particles which pass through a space between the ridge components 10, which represent charged particles possessing a high energy with which the charged particles can reach a deep position below a surface 26 of a human body being treated. On the other hand, since charged particles intercepted by the shielding element 7 are shielded, the charged particle beam passing through a ridge component 10 partially covered by a shielding element 7 includes charged particles of a low energy, which stop at a shallow position below the surface of a human body, in contrast to the charged particle beam passing through a ridge component 10 without a shielding element 7. That is, a charged particle beam passing through a ridge component 10 covered by a shielding element 7 has a narrower range of irradiation in comparison with a charged particle beam passing through a ridge component 10 without a shielding element 7 mounted therein.

Thus, by suitably arranging the above-mentioned ridge components 10 with the shielding elements 7 in the ridge filter 2, it is possible to change the ranges of irradiation at various parts of a target, corresponding to places in the ridge filter 2 at which ridge components 10 with shielding elements 7 are arranged.

In this embodiment, the ridge components 10 with shielding elements 7 are arranged at corresponding places in the ridge filter 2 in accordance with the three-dimensional shape of the diseased part 6. The ridge components 10 without shielding elements 7 are arranged at a central region in the vicinity of the central axis 16 of the ridge filter 2, through which the charged particle beam to be irradiated on a region 6a of large thickness in the diseased part 6 passes. On the other hand, the ridge components 10 with shielding elements 7 mounted thereon are arranged at a peripheral region spaced from the central axis of the ridge filter 2.

In the following, the dose rate distribution of a charged particle beam irradiated in a region containing the diseased part 6 in a human body will be explained.

Figure 5:
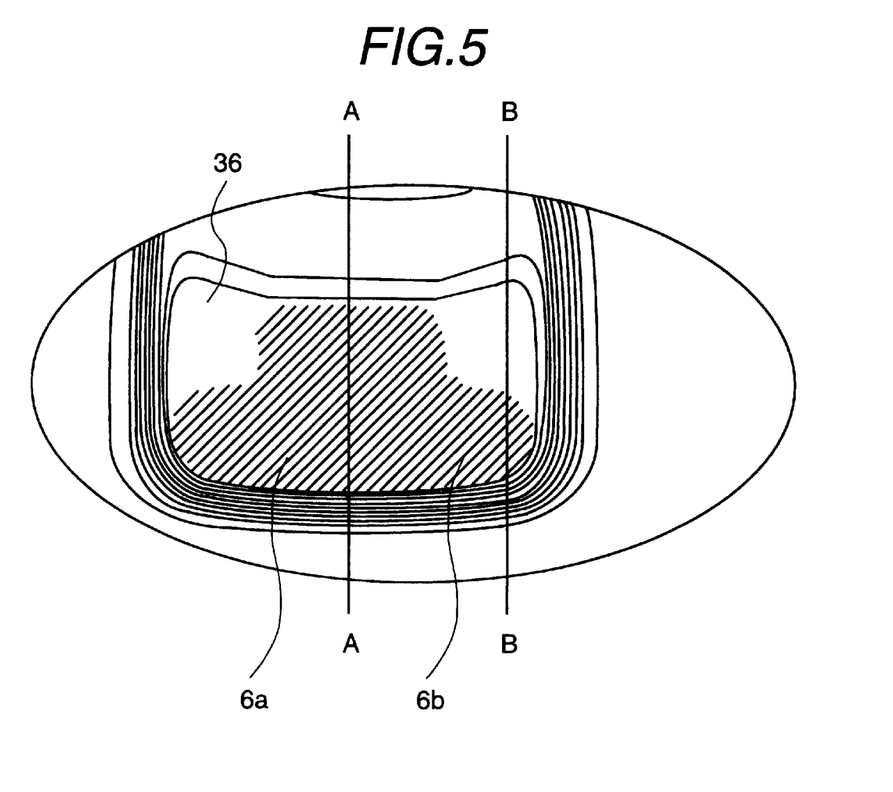
FIG. 5 is a contour graph of the dose rate in a horizontal cross section of a diseased part onto which a charged particle beam is irradiated by a conventional irradiation method.

At first, the dose rate distribution for a case in which the charged particle beam is irradiated by a conventional irradiation method in which a conformal irradiation is not adopted and the shielding elements 7 are not used at all will be explained. FIG. 5 is a contour graph of the dose rate distribution in a horizontal cross section of the region containing the diseased part 6. Since the energy distribution of the charged particle beam which has passed through the ridge filter 2 is spatially uniform in the region 36 of the target, if the energy range of the charged particle beam is determined according to the thick region 6a in the diseased part 6, the dose rate in the thin region 6b will be almost the same as that of the thick region 6a. That is, the beam will not be irradiated in accordance with the three-dimensional shape of the diseased part 6 using the conventional irradiation method.

Next, consideration will be given to the case wherein the charged particle beam is irradiated by the charged particle beam irradiation system of this embodiment, in which some of the ridge components 10 are provided with shielding elements 7. The dose rate distribution will be explained with reference to FIG. 6, which is a contour graph of the dose rate distribution in a horizontal cross section of a region containing the diseased part 6, with reference to FIG. 7, which is a graph of a dose rate distribution in a vertical cross section along line A—A in FIG. 6, and with reference to FIG. 8, which is a graph of a dose rate distribution in a vertical cross section along line B—B in FIG. 6.

Figure 7:
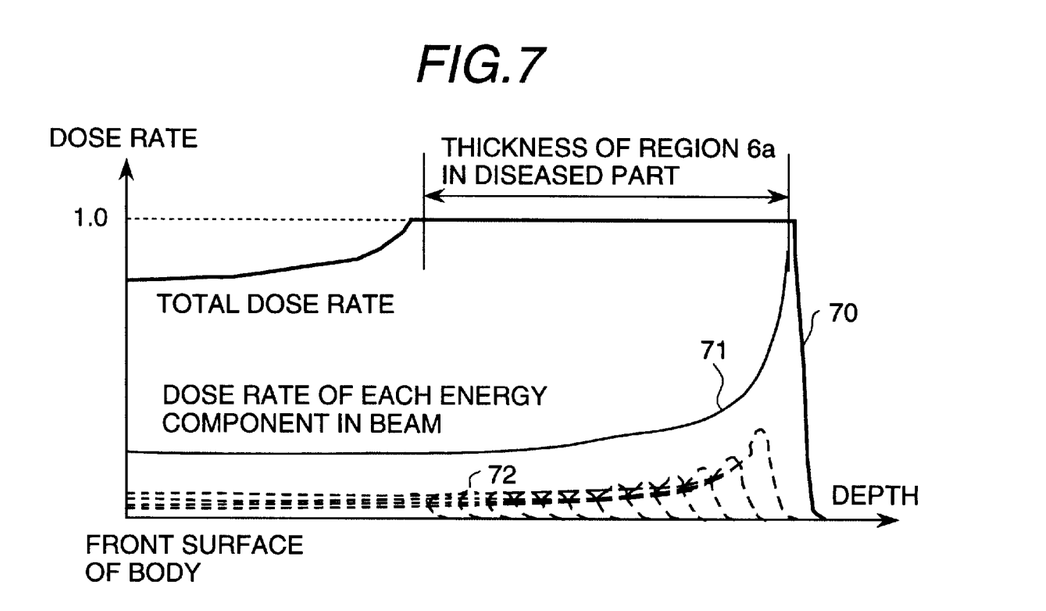
FIG. 7 is a graph showing a dose rate distribution in a vertical cross section along line A—A in FIG. 6.
Figure 8:
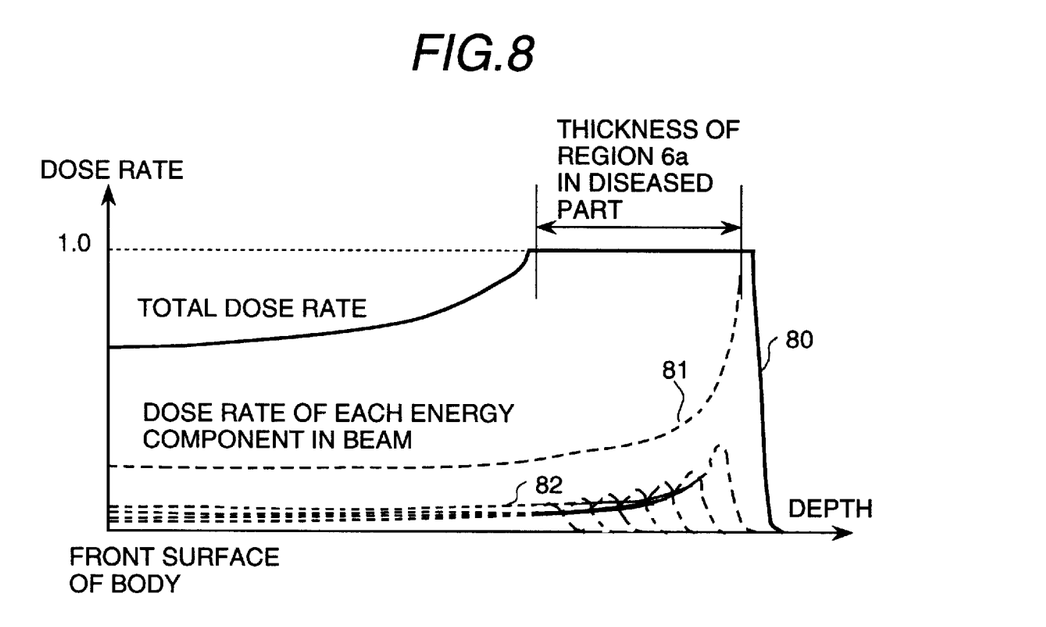
FIG. 8 is a graph showing a dose rate distribution in a vertical cross section along line B—B in FIG. 6.

The charged particle beam irradiated onto a region in the vicinity of the vertical cross section along the line A—A is the beam passing through the region in which the ridge components 10 without the shielding elements 7 are arranged in the ridge filter 2. On the other hand, the charged particle beam irradiated on a region in the vicinity of the vertical cross section along the line B—B is the beam passing through the region in which the ridge components 10 covered with the shielding elements 7 are arranged in the ridge filter 2. In FIG. 7 and FIG. 8, the respective solid lines 70 and 80 represent the total dose rate distribution caused by the charged particle beam passing through the whole ridge component 10 in each of the cases shown in FIG. 7 and FIG. 8. Further, each dashed line indicates the dose rate distribution caused by the beam passing through a tier (step) formed in the sides of the ridge component 10. The total dose rate distribution curve indicated by each solid line is equal to the superimposition of the close rate distribution curves for the respective energy components of the whole charged particle beam. Further, in FIG. 7 and FIG. 8, the lines 71 and 81 indicate the close rate distribution curves which represent a condition in which a charged particle beam reaches the deepest position of the diseased part 6, typically produced by the beam passing through the space between the ridge components 10. Since each shielding element 7 is attached at only the top part of each ridge component 10, the attached shielding element 7 does not affect the charged particle beam which passes through the space between ridge components 10 and reaches the deep position of the diseased part 6. Therefore, the dose rate at the deepest position in FIG. 7 is the same as that in FIG. 8.

In FIG. 7, the dashed line 72, showing a charged particle beam that stops at a shallow position in the diseased part 6, indicates the dose rate distribution caused by the charged particle beam which has passed through the vicinity of the top parts of the respective ridge component 10 in the ridge filter 2. Since the beam irradiated on the region in the vicinity of the vertical cross section along the line A—A includes a charged particle beam of low energy causing a low dose rate curve, for example, the dashed curve 72 indicating that the beam stops at a shallow position, the range of the maximum total dose rate (1.0) shown by the solid line 70 almost coincides with the thickness along the line A—A in the diseased part 6.

Figure 6:
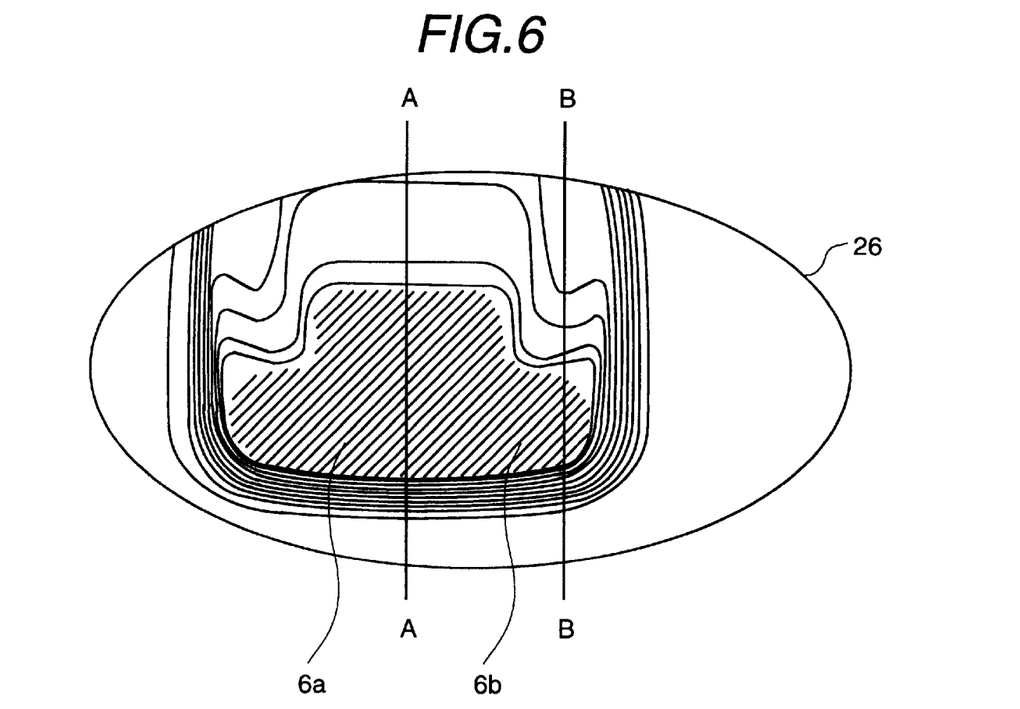
FIG. 6 is a contour graph of the dose rate in a horizontal cross section of a diseased part onto which a charged particle beam is irradiated by the charged particle beam irradiation system shown in FIG. 1.

In FIG. 8, the dashed line 82, showing a beam that stops at a shallow position of the diseased part 6, indicates the close rate distribution caused by a charged particle beam which passed through a tier part 74 of each ridge component 10 in the ridge filter 2 shown in FIG. 4, which is not covered with a shielding element 7. Since the charged particle beam irradiated on the part in the vicinity of the vertical cross section along the line B—B does not include charged particles of a low energy, which stop at a shallow region below the surface 26 of the human body being treated, the range of the maximum total dose rate (1.0) is narrower than that caused by charged particles irradiated on the region in the vicinity of the vertical cross section along the line A—A, and almost coincides with the thickness of the thin region 6b along the line B—B in the diseased part 6. Thus, as shown in FIG. 6, the dose rate in the region 36 of the target existing at the more shallow side of the thin region 6b is lower than that in the area of the thick region 6a of the diseased part 6, and so the dose rate in the diseased part 6 is uniform. Moreover, the shape of the region in which the dose rate is uniform substantially coincides with the shape of the diseased part 6.

In accordance with this embodiment, by forming the ridge filter 2 with the ridge components 10 and the shielding elements 7 attached at a part of the ridge components 10, it is possible to distribute a charged particle beam easily according to the three-dimensional shape of the diseased part 6. Further, by changing the area of the ridge component 10 which is covered by each shielding element 7, it is possible to adjust the dose rate distribution of a charged particle beam in the beam direction. In this embodiment, although the shielding elements 7 attached at the ridge components 10 are provided for a diseased part 6 having a two-step thickness, it is possible to satisfy an irradiation requirement for diseased parts of a complicated shape having a multi-step thickness by providing plural types of shielding elements 7 which cover the respective ridge components 10 with different area ratios.

Further, in this embodiment, since a spread or reduction in area of the beam in the beam direction, or an adjustment of the energy range in the beam, is not performed by the collimator 4, controlling the charged particle beam irradiation system is simple. Moreover, even in the case where a multi-leaf collimator is used, since the range of irradiation can be adjusted, controlling the charged particle beam irradiation system is simple.

Furthermore, although the shielding element 7 is attached at the top part of the ridge component 10, it is possible to attach the shielding element 7 at the bottom part of the ridge component 10. Further, a conic ridge component can be used for each of the ridge components 10. For a conic ridge component, a cylindrical shielding element is used for each of the shielding elements 7. Although the collimator 4 is used in this embodiment, a multi-leaf collimator is also applicable. Moreover, as a beam spreading method, a method which uses a particle scattering means, a method of scanning a beam, and so forth, are applicable.

In the following, a second embodiment according to the present invention will be explained.

Figure 9:
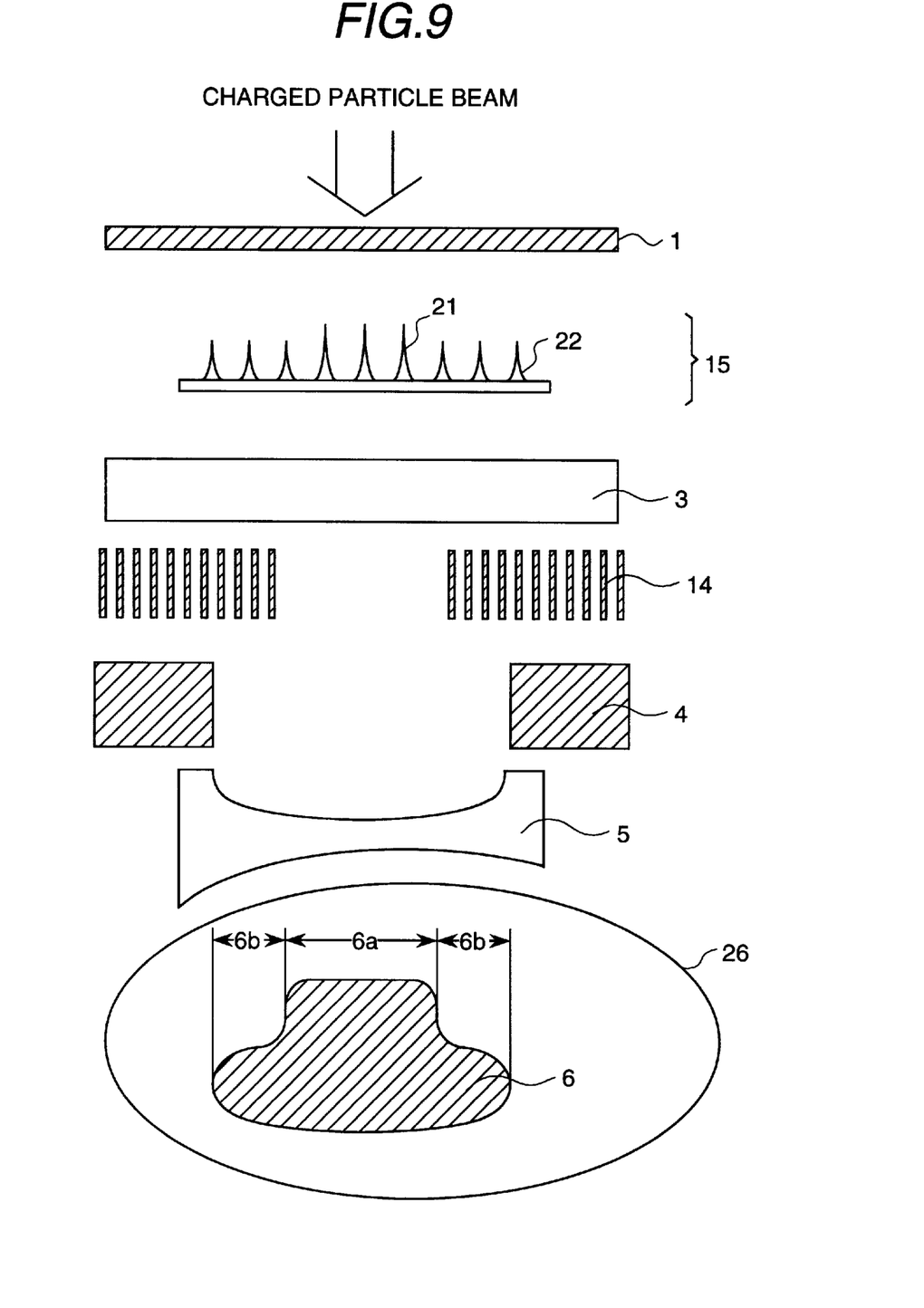
FIG. 9 is a schematic diagram showing the composition of a charged particle beam irradiation system forming a second embodiment of the present invention.

FIG. 9 is a schematic diagram showing the composition of a charged particle beam irradiation system forming a second embodiment of the present invention. Mainly, the differences between this embodiment and the first embodiment will be explained. In this embodiment, an uneven ridge filter 15 is used. The uneven ridge filter 15 is composed of high ridge components 21 arranged at a central part of the filter 15 and low ridge components 22 arranged at a peripheral part of the uneven ridge filter 15, corresponding to a diseased part 6 having a large thickness at its central part and the smeller thickness at its peripheral part. Downstream of the range shifter 3, a shielding device 14 is provided, which includes a plurality of shielding elements for shielding a part of the charged particle beam, corresponding to the thin region 6b in the diseased part 6.

Figure 10:
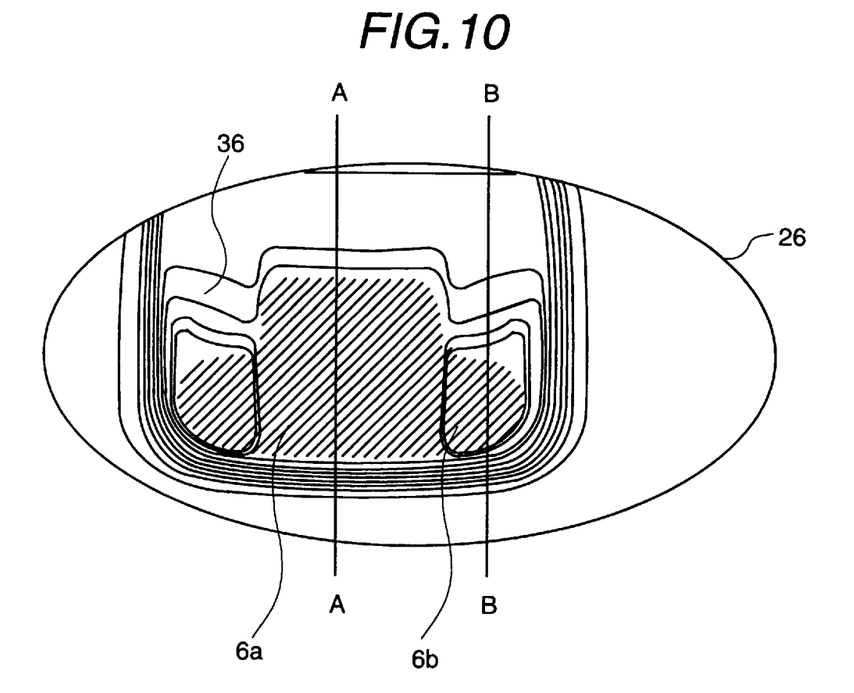
FIG. 10 is a contour graph of the dose rate in a horizontal cross section of a diseased part onto which a charged particle beam is irradiated by a conventional irradiation method in which an uneven ridge filter is used.
Figure 11:
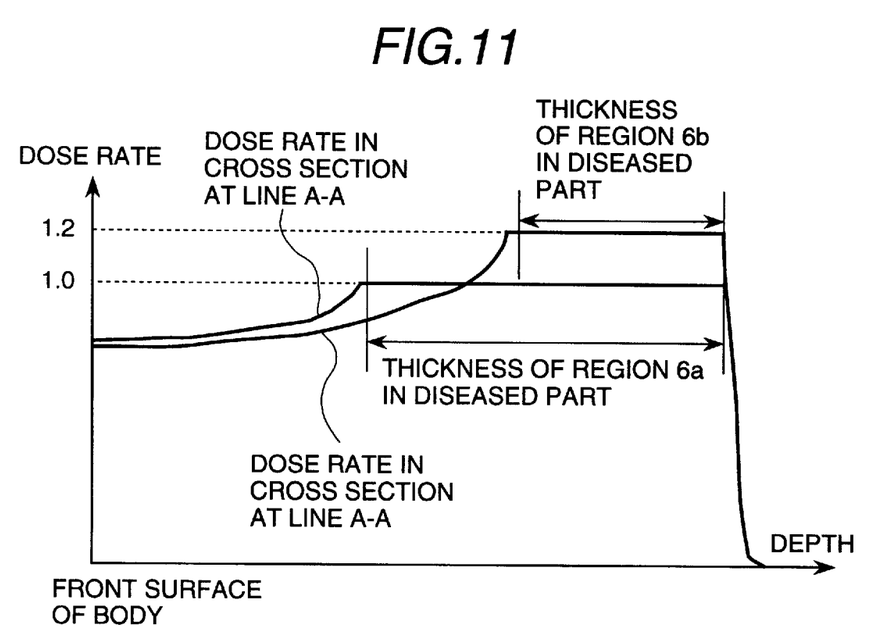
FIG. 11 is a graph of a dose rate distribution in a horizontal cross section along each of line A—A and line B—B in FIG. 10.

At first, the dose distribution caused by a conventional charged particle beam irradiation system in which the shielding device 14 is not used, but only the uneven ridge filter 15 is provided, will be explained. FIG. 10 is a contour graph of the dose distribution in a horizontal cross section of the diseased part 6. FIG. 11 shows a graph of the dose distribution in a horizontal cross section along each of line A—A and line B—B in FIG. 10.

Since the height of the ridge components 21 arranged at the central part of the uneven ridge filter 15 is high, the energy range of a charged particle beam passing through the central part is wide. On the other hand, since the height of the ridge components 22 arranged at the peripheral part of the uneven ridge filter 15 is low, the energy range of a charged particle beam passing through the peripheral part is narrower then the former energy range. Therefore, the dose due to irradiation of the target by the charged particle beam passing through the peripheral part is higher than that due to irradiation of the target by the charged particle beam passing through the central part.

Consequently, with a one time irradiation, it is impossible to equalize the dose in the thick region 6a relative to that in the thin regions 6b in the diseased part 6. As shown in FIG. 11, assuming that the dose due to irradiation of the charged particle beam passing through the central part in the uneven ridge filter 15 is 1.0 and the dose due to irradiation of the charged particle beam passing through the peripheral part is 1.2, in order to realize a uniform dose distribution in the whole diseased part 6, it is necessary to irradiate a charged particle beam only on the thick region 6a so that the dose in the thick region 6a attains the planned dose of 1.2 by adjusting the collimator 4 after the dose in the thin region 6b reaches the planed dose of 1.2.

Next, the dose distribution caused by the embodiment of the present invention using the shielding device 14 will be explained. Since the energy distribution of the charged particle beam passing through the central part of the uneven ridge filter 15 is wider because of the higher ridge components 21, the dose in the thick region 6a of the diseased part 6 is lower, similar to the irradiation produced by the conventional method.

On the other hand, since the charged particle beam passing through the peripheral part of the uneven ridge filter 15 does not include charged particles of a lower energy, which stop at a shallow region below the surface 26 of a human body being treated, because of the lower ridge components 22, the energy distribution of this charged particle beam is narrower than that of the charged particle beam in the part in which the high ridge components 21 are provided. However, since a part of the charged particle beam is absorbed by the shielding device 14 arranged downstream of the range shifter 3, the dose in the thin region 6b of the diseased part 6 becomes lower in comparison with that due to irradiation without the shielding device 14. Thereupon, assuming that the dose in the thin region 6b due to the irradiation without the shielding device 14 is 1.2, it is possible to realize a uniform dose distribution in the whole diseased part 6, by using the shielding device 14 to absorb approximately 17% of the charged particle beam. That is, the contour graph of the dose rate in the human body according to this embodiment is almost the same as that shown in FIG. 6. Therefore, in accordance with this embodiment, it is possible with a one time irradiation to realize a uniform dose distribution in the diseased part 6.

Figure 12:
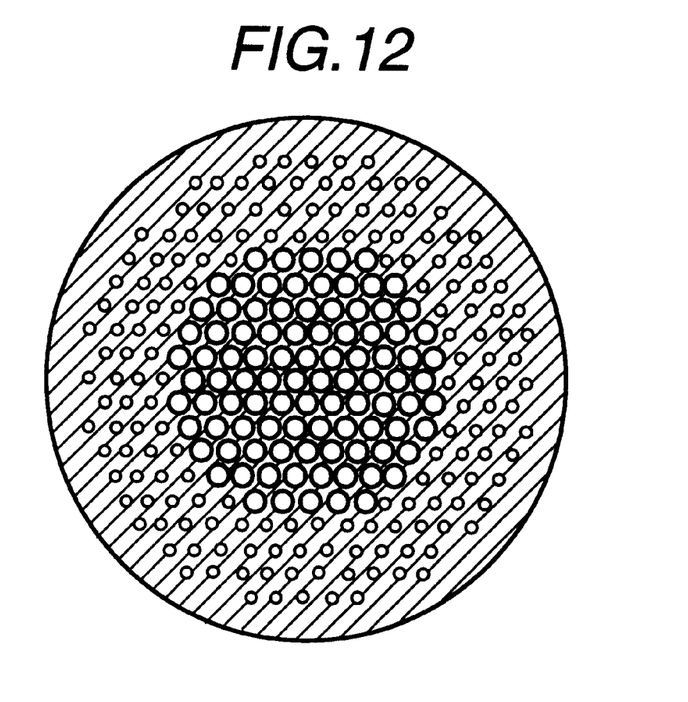
FIG. 12 is a front view showing sets of shielding elements having different beam shielding ratios.

Further, in order to target a diseased part 6 having a complicated shape with a multi-tier thickness, by using a conventional irradiation method, it has been necessary to perform irradiation for each tier by adjusting the collimator 4, that is, it has been necessary to perform irradiation several times. On the other hand, by using the shielding device 14 shown in FIG. 12, in which a plurality of shielding elements having different shielding rates are arranged, it is possible to obtain a dose distribution in the diseased part 6 which is uniform, according to the three-dimensional shape of the diseased part 6.

Further, in this embodiment, since a spread or reduction of the beam in the beam direction, or an adjustment of the energy range in the beam, is not performed by the collimator 4, controlling the charged particle beam irradiation system is simple. Moreover, even in the case where a multi-leaf collimator is used, since the range of irradiation can be adjusted, controlling the charged particle beam irradiation system is simple.

Furthermore, as mentioned in the explanation of the first embodiment, a conic ridge component can be used as each ridge component 10. For a conic ridge component, a cylindrical shielding element is used as each shielding element 7. Although the collimator 4 is used in this embodiment, a multi-leaf collimator is also applicable. Moreover, as a beam spreading method, a method which uses a particle scattering means, a method which scans a beam, and so forth, can be used.

Figure 13:
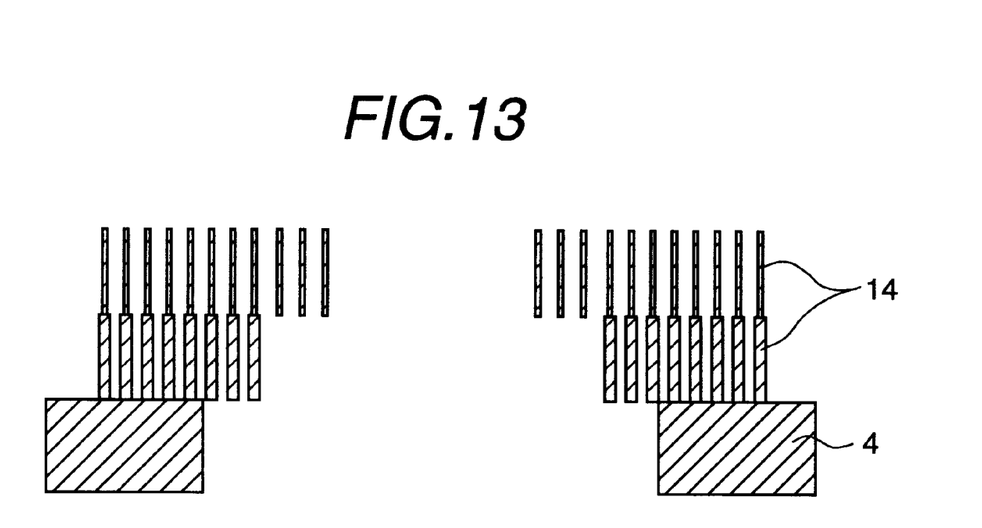
FIG. 13 is a horizontal view in the beam direction, of sets of shielding elements having different beam shielding ratios, which are arranged in order in the beam direction.
Figure 14:
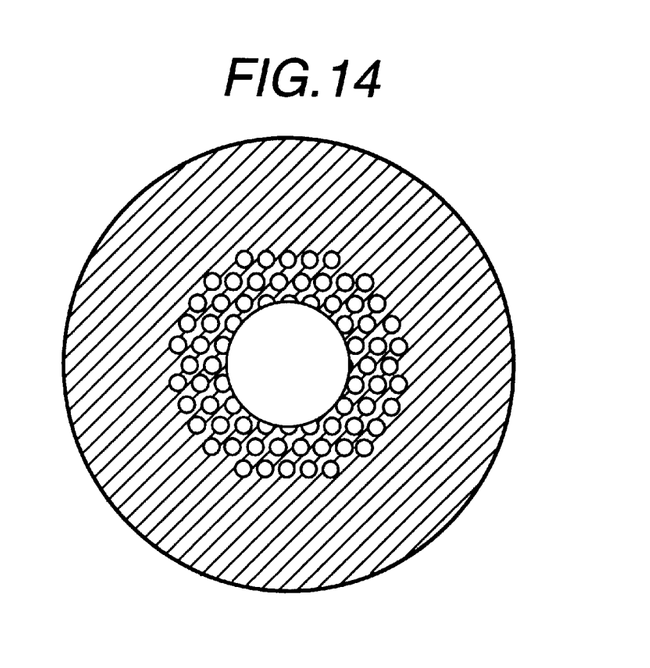
FIG. 14 is a front view showing another set of shielding elements having different beam shielding ratios, which possesses a collimator function also.
Figure 15:
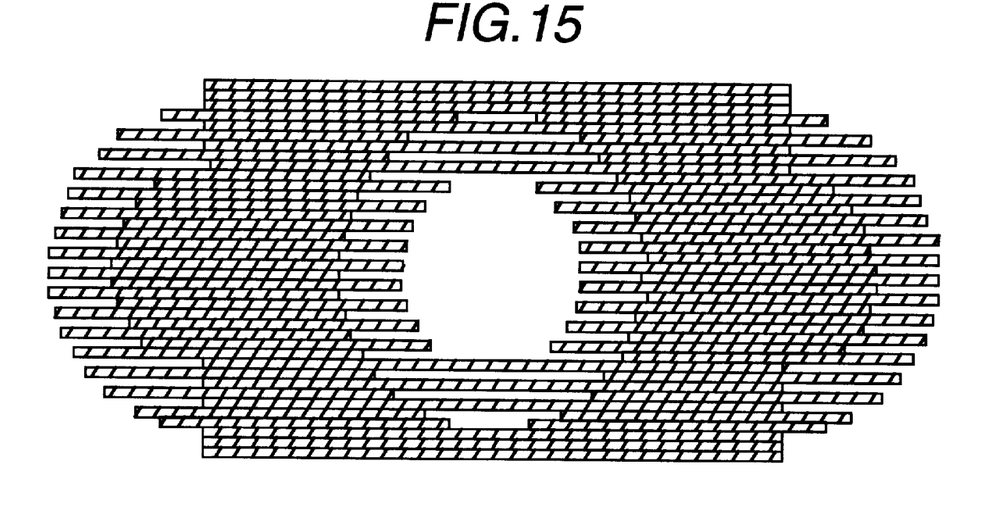
FIG. 15 is a front view showing still another set of shielding elements having different beam shielding ratios, which possesses a multi-leaf collimator function also.

Moreover, as shown in FIG. 13, it is possible to place shielding devices 14 having a plurality of stages arranged in order in the direction of the upper stream to the lower stream. Further, it is possible to use a shielding device as well as a collimator, as shown in FIG. 14, or to use a shielding device 14 in the form of a multi-leaf collimator, as shown in FIG. 15.

According to the present invention, by using a system of simple composition, it is possible to irradiate a charged particle beam onto a target in accordance with the three-dimensional shape of the target, and further, to realize a uniform distribution of the dose of radiation on the target.

What is claimed is:

1. A charged particle beam irradiation system for irradiating a charged particle beam, which includes a plurality of charged particles in an energy range, onto a target having a non-uniform depth distribution in its cross section in a charged particle beam irradiation direction, and which further includes a plurality of ridge components and shielding elements to shield a part of said charged particle beam in an area corresponding to a comparatively thin region in said target.

2. A charged particle beam irradiation system according to claim 1, wherein said shielding elements are composed and arranged so that a difference between a maximum energy and a minimum energy of charged particles in a charged particle beam irradiated onto a comparatively thick region of said target is larger than a difference between a maximum energy and a minimum energy of charged particles irradiated onto a comparatively thin region of said target.

3. A charged particle beam irradiation system according to claim 2, wherein said shielding elements are attached to a part of said ridge components, said charged particles irradiated onto said comparatively thin region of said target passing through said part of said ridge components.

4. A charged particle beam irradiation system, which includes a ridge filter, for irradiating a charged particle beam, which includes a plurality of charged particles in an energy range, onto a target having a non-uniform depth distribution of its cross section in a charged particle beam irradiation direction, wherein said ridge filter which is placed along a trajectory of said charged particle beam includes a plurality of ridge components having different values of height, and a plurality of shielding elements to shield a part of said charged particle beam passing through comparatively low ridge components of said plurality of said ridge components.

5. A charged particle beam irradiation system for irradiating a charged particle beam, which includes a plurality of charged particles in an energy range, onto a target having a non-uniform depth distribution of its cross section in a charged particle beam irradiation direction, further including beam adjustment means for adjusting said charged particle beam so that a difference between a maximum energy and a minimum energy of charged particles in a charged particle beam irradiated onto a comparatively thick region of said target is larger than a difference between a maximum energy and a minimum energy of charged particles irradiated onto a comparatively thin region of said target, and a particle density of said charged particles in said charged particle beam irradiated onto said comparatively thick depth region is higher than a particle density of said charged particles irradiated onto said comparatively thin region.

6. A charged particle beam irradiation method of irradiating a charged particle beam, which includes a plurality of charged particles in an energy range, onto a target having a non-uniform depth distribution of its cross section in a charged particle beam irradiation direction, said method comprising the steps of:

arranging shielding elements at a part of ridge components which compose a ridge filter;

placing said ridge filter along a trajectory of said charged particle beam; and irradiating said charged particle beam through said ridge filter onto said target.

\* \* \* \* \*